(12) United States Patent
Bublewitz et al.

(10) Patent No.: US 6,313,190 B1
(45) Date of Patent: Nov. 6, 2001

(54) ADDITION CROSS-LINKING, TWO-COMPONENT SILICONE MATERIAL WITH HIGH SHORE HARDNESS AND HIGH MODULUS OF ELASTICITY

(75) Inventors: Alexander Bublewitz; Jens-Peter Reber, both of Herborn (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 09/171,479

(22) PCT Filed: Apr. 18, 1996

(86) PCT No.: PCT/EP96/01623

§ 371 Date: Mar. 1, 1999

§ 102(e) Date: Mar. 1, 1999

(87) PCT Pub. No.: WO97/40102

PCT Pub. Date: Oct. 30, 1997

(51) Int. Cl.[7] ........................................................ A61K 6/10
(52) U.S. Cl. ............................................. 523/109; 524/588
(58) Field of Search .............................. 524/588; 523/109

(56) References Cited

FOREIGN PATENT DOCUMENTS

| | | |
|---|---|---|
| 0305073 | 3/1989 | (EP) . |
| 0522341 | 1/1993 | (EP) . |
| 0579132 | 1/1994 | (EP) . |
| 579 132 * | 1/1994 | (EP) . |
| 9317654 | 9/1993 | (WO) . |

* cited by examiner

Primary Examiner—Margaret G. Moore
(74) Attorney, Agent, or Firm—Friedrich Kueffner

(57) ABSTRACT

Addition cross-linking two-component silicone materials Addition cross-linking two-component silicone materials on polysiloxane base, especially for the use in dental medicine and dental technique contain, so as to obtain a product with a high Shore D hardness and a high modulus of elasticity, organopolysiloxanes with two vinyl groups in the molecule, organohydropolysiloxanes with two or more SiH groups in the molecule, catalysts for the acceleration of the hydrosilation reaction, reinforcing material, non-reinforcing material, eventually dyestuff, eventually moisture binder, eventually organopolysiloxanes with more than two vinyl groups in the molecule, eventually inhibitors for the adjustment of reactivity, eventually vinyl group containing solid or liquid MQ-resins, eventually compounds made of organopolysiloxanes and reinforcing filling material, eventually tensides, emulsifying agents and stabilizing agents, eventually radio-opaque substances and eventually $H_2$ absorbing or adsorbing substances and substances which eliminate or reduce the $H_2$ development.

31 Claims, 2 Drawing Sheets

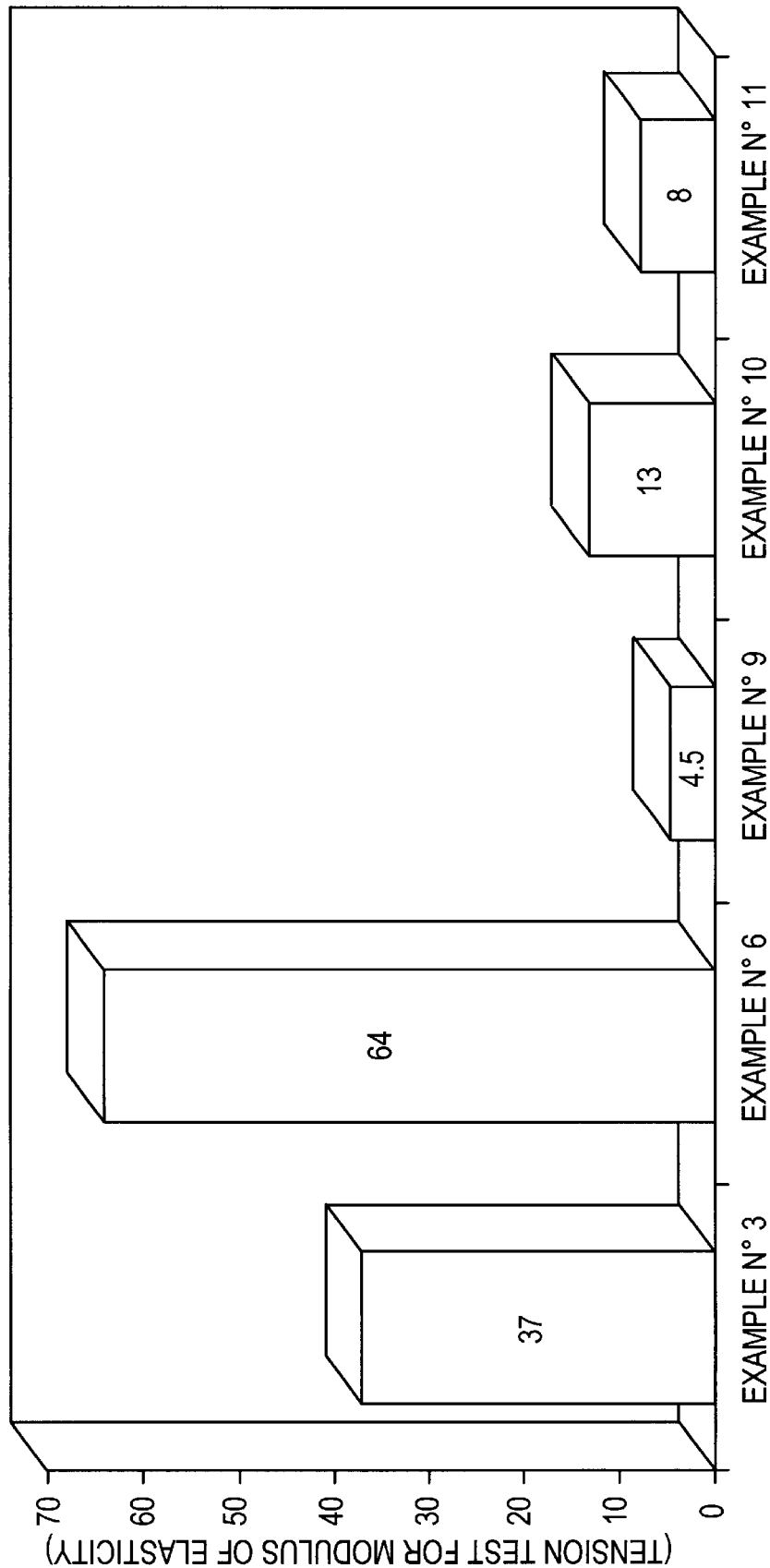

ADDITION CROSS-LINKING, TWO-COMPONENT SILICONE MATERIAL WITH HIGH SHORE HARDNESS AND HIGH MODULUS OF ELASTICITY

BACKGROUND OF THE INVENTION

1. Field of the Invention

There is a need in many proceedings in dental medicine and dental technique for materials which pass over from a viscous state to a particularly hard final state. Especially for the keying, fixing, positioning, repair, transfer and remounting, there is the demand on a high final hardness of the material used. One of the most important fields of application is the bite impression.

2. Description of the Related Art

For the bite impression, the positional relation of both jaws the one to the other has to be precisely fixed. The resulting bite impression serves as a base for the work of the dental laboratory technician to transfer the bite situation specific to the patient to the pattern situation. Bite impressions are made by the dentist in almost all fields. An appropriate bite impression material has to meet the following requirements.

For a precise impression, it is important that the material does not allow any displacement in vertical and horizontal direction. Therefore, a particularly high final hardness and a low elasticity of the material is a main requirement. Moreover, the high hardness is a condition for a good processing of the impression with a milling cutter or a scalpel. For a checking of the right bite impression in the patient's mouth, it is desirable to be able to break off excess material purposefully. For the impression, a particularly short retention time in the mouth as well as a sufficient whole processing time are required to avoid a displacement of the jaws during the setting phase. The dimensions of the material may not vary during the transport from the dental pratice to the dental laboratory and later on. The user wants an easy handling when metering, mixing and applying as well as a storage stability as long as possible.

It is known to use addition cross-linking silicones for bite impressions; they have a higher final hardness and a lower strain compared with the silicones usually used in dental medicine.

The products on the market reach a Shore A final hardness of 70 to 90.

Therefore, for the indication bite impression a substantial increase of the final hardness or of the modulus of elasticity is desirable for a better precision.

The A-silicone which will be described below, which has a particularly high final hardness, brings substantial advantages for example for the following indications
sprayable material for bite impressions
material for the coating of the biting fork or of the impressing plates for impression
keying material, for example for intraoral support peg impressions
transfer of brackets in orthodontics
remounting of ceramic, cast or plastic fillings to grind in the occlusion on the pattern
underlining silicone which becomes hard
pattern material for the fabrication of inlays/onlays.

The above mentioned known addition cross-linking silicones are made of two components which chemically cross-link over a noble metal catalyzed hydrosilylation.

The A and B components are adjustable in various viscosities (fluid, moderately fluid, viscous, kneadable) and mixture ratios (generally 1:1). The mixing of the A and B components may be completed according to weight and volume and is carried out by appropriate metering and mixing devices as, for example, extruded length metering and manual mixing, cartridge system with static mixer and electrically/mechanically operated mixing apparatus. After having metered and mixed the A and B components, the resulting homogeneously mixed paste is applied during the whole processing time with appropriate aids into the patient's mouth. After the curing of the material (retention time in the mouth), it is removed from the patient's mouth and further processed as required.

According to the state of the art, bite impression materials on the base of addition cross-linking silicones have the following raw material composition
a) organopolysiloxanes with two or more vinyl groups in the molecuie and a viscosity between 100 and 350 000 MPA·s,
b) organopolysiloxanes of the general formula:

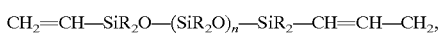

$$CH_2=CH—SiR_2O—(SiR_2O)_n—SiR_2—CH=CH—CH_2,$$

"R" meaning similar or different monovalent, eventually substituted hydrocarbon rests, free from aliphatic multiple compounds, and "n" an integral number with a value from 10 to 20,
c) low molecular vinyl and ethoxyl group containing MQ-resins,
d) organohydrogenpolysiloxanes (SiH cross-linking agent) with two or more SiH groups in the molecule,
e) catalysts for the acceleration of the hydrosilylation reaction,
f) dyestuff,
g) reinforcing filling material (optionally also surface treated, precipitated and pyrogenically fabricated),
h) compounds made of polydimethylsiloxanes and a.m. reinforcing filling material,
i) non-reinforcing filling material (optionally also surface treated).

From EP-A-0 522 341 we know a transparent material on the base of addition cross-linking polysiloxanes which is preferably used for the bite impression in dental technique to allow a checking of the adjustments or positions because of their transparentness, for example by light polymerization. According to this, the object is at ambient temperatures hardenable compositions on the base of polysiloxane which cross-link according to the addition process and which contain, besides organopolysiloxanes with two or more vinyl groups in the molecule, organohydrogenpolysiloxanes with two or several Si-H-groups in the molecule, a catalyst for the acceleration of the addition reaction and, eventually, dyestuff, whereby the latter prejudice the desired transparentness, still compounds of microdispersed, active filling material in silicone oil, short-chain organopolysiloxanes with two or several vinyl groups in the molecule and optionally a low molecular vinyl and ethoxyl group containing QM-resin, in which organopoiysiloxanes with two or more vinyl groups in the molecule are homogenously soluble, which has first a vinyl group content of 0.5 8 mMol/g and second which is made of $SiO_{4/2}$-, $RO_{1/2}$- and $R_3SiO_{1/2}$ units and R is a methyl, vinyl, phenyl and ethyl group and has a ethoxyl group content of less than 4 mMol/g, whereby the organohydrogenpolysiloxanes with two or several Si-H-groups in the molecule are contained in the base paste and the catalyst for the acceleration of the addition reaction in the catalyst paste. Base and catalyst paste should stand out for a high temperature stability with respect to viscosity. The bite impressions fabricated with this mass should have a high hardness, a high transparentness and resistance to tearing for a low strain. The QM-resins which are set in here must be so low molecular that they are transparently soluble in the vinyl end stopped polydimethylsiloxanes so as to obtain the desired transparentness of the bite impressions. The products which are obtained here do not have a high Shore D hardness (10 to 19) and a high modulus of elasticity (about 5 to 9 Mpa).

SUMMARY OF THE INVENTION

The present invention aims at creating addition cross-linking two-component silicone materials with a high Shore D hardness and a high modulus of elasticity and thus at obtaining compositions of addition cross-linking two-component silicone materials which can be used particularly advantageously in dental medicine and dental technique when vulcanized because of their high Shore D hardness and their high modulus of elasticity compared to the known A-silicones for various problem definitions which are not yet solved in a satisfying way.

The Shore D hardness required here of more than 35 and the modulus of elasticity of more than 20 MPa shall be reached while maintaining the other mechanical properties and the working properties with respect to appropriately processable viscosities/consistencies with the a.m. metering and mixing systems, quick setting behaviour, flexibility, workability, removability, flow behaviour during the processing time and eventually smooth surface finish. The formulation of the contents will have a sufficient storage stability in the corresponding primary packing, for example cartridge or tube, whereby by storage stability in this context we understand for example the maintaining of the features of performance before and during the vulcanization with respect to the viscosity/consistency of the single components and the mixture as well as of the setting characteristic curve over at least 12 months and after the vulcanization with respect to the Shore hardness, the elasticity and the modulus of elasticity over at least one month.

The present invention solves this problem and meets the above mentioned requirements with the following composition of the contents:
a) organopolysiloxanes with two or more vinyl groups in the molecule
b) organohydropolysiloxanes with two or more SiH groups in the molecule
c) catalysts for the acceleration of the hydrosilylation reaction
d) reinforcing filling material
e) non-reinforcing filling material
f) optionally dyestuff
g) optionally moisture binder
h) optionally organopolysiloxanes with more than two vinyl groups in the molecule
i) optionally inhibitors for the adjustment of reactivity
j) optionally vinyl group containing solid or liquid MQ-resins
k) optionally compounds made of organopolysiloxanes and reinforcing filling material
l) optionally tensides, emulsifying agents and stabilizing agents
m) optionally radio-opaque substances
n) optionally $H_2$-absorbing or adsorbent substances and substances which eliminate or reduce the $H_2$-development.

The hereunder mentioned advantages of the silicone material according to the invention are represented for comparison in the tables 1 and 2.

The silicone material according to the invention stands out especially for a high Shore D hardness and for a high modulus of elasticity at vulcanized state.

Because of the high Shore D hardness, it is possible to obtain a purposeful crushability of the excess silicone material which is hardened in the mouth so that a visual checking of the bite print, contrary to EP-A-0522 341, is possible even with not transparent silicone materials according to the invention.

The high Shore D hardness or the high modulus of elasticity makes an advantageous processing of the bite print with a milling cutter possible.

Furthermore, because of the high Shore D hardness, a precise relation of the upper and lower jaw patterns the one to the other is possible, since the very hard silicone material does not allow any displacement in vertical and horizontal direction.

Unlike bite impression materials with lower Shore hardness, there is, with the silicone material according to the invention, no compressibility and no elastic hysteresis because of its low elasticity (high modulus of elasticity) when positioning in the articulator. In this way, a precise print and transfer to the pattern is guaranteed.

Furthermore, the silicone material according to the invention stands out, besides a practice-oriented processability and a good flow behavior during the processing time, for a quick setting in the mouth of the patient which is not harmful for him (retention time of 90 seconds in the patient's mouth for a processing time of at least 30 seconds).

Because of the composition of the silicone material according to the invention, it is possible to avoid an extremely high platinum content of more than 100 ppm as required with the use of very short chain inhibitory vinyl containing silicone oils which cause a restricted storage stability with a further prejudice to the setting properties.

Furthermore, the composition of the silicone material according to the invention on the base of organopolysiloxanes with two vinyl groups in the molecule and a viscosity of 21 to 99 mpa·s has, despite of the high vinyl content, no inhibitory effect on the rate of vulcanization. Vulcanizations with "snap effect" are performed in relation with the SiH cross-linking agent and the platinum catalyst.

Because of the high rate of vulcanization under mouth conditions, the high risk of shifting during the bite impression in the patient's mouth is minimized, thus finally increasing the precision of the bite impression.

BRIEF DESCRIPTION OF THE DRAWING

FIG. 2 is a bar diagram showing a comparison of moduli of elasticity of several sample materials.

DETAILED DESCRIPTION OF THE INVENTION AND BEST WAY TO PERFORM THE INVENTION

Figure 1:
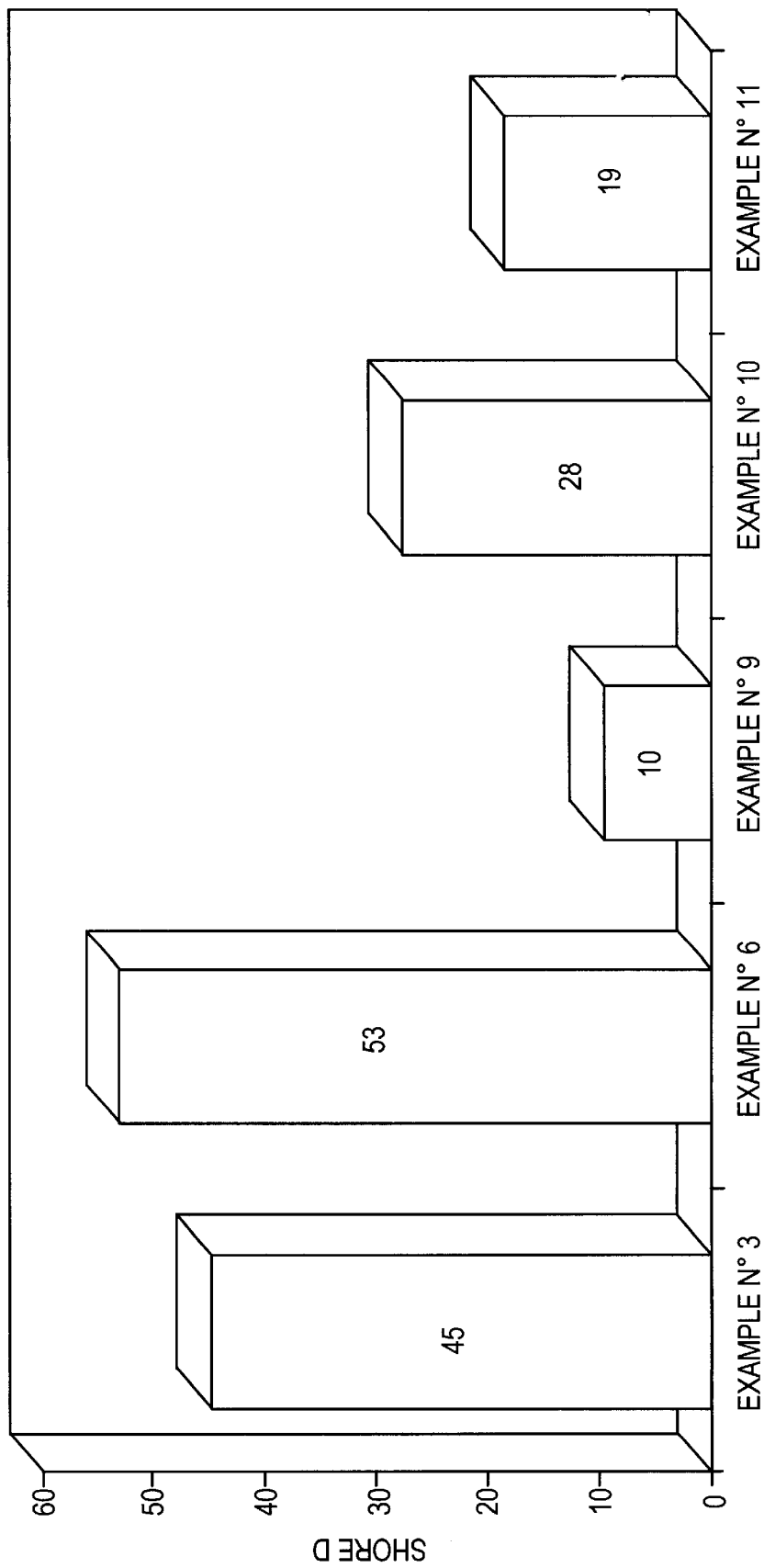
FIG. 1 is a bar diagram showing a comparison of the Shore D Hardness of several sample materials.

The organopolysiloxanes a) with two vinyl groups in the molecule and a viscosity between 21 and 99 mPa·s comprise substances with the general formula

$$CH_2=CH-SiR_2O-(SiR_2O)_n-SiR_2-CH=CH_2$$

in which

R=alkyl (for example methyl, ethyl, isopropyl), aryl (for example phenyl, naphtyl, tolyl, xyiyl), aralkyl (benzyl, phenylethyl) and halogen substituted alkyl and aryl groups (for example 3,3,3-trifluoropropyl, chlorophenyl, difluorophenyl), cyanoalkyl, cycloalkyl and cycloalkenyl. Preferably R=methyl.

n=a whole number with a value between 21 and 69, whereby "n" represents theoretically calculated values which are calculated from the experimentally determined vinyl content, assuming that two vinyl groups are contained in a molecule and R=methyl.

The organohydrogensiloxane components b) serve as cross-linking agents and are polyalkyl, polyaryl and polyalkylaryl as well as polyhalogenalkyl, polyhalogenaryl and polyhalogen-alkylaryl siloxanes which have at least two hydrogen atoms combined with silicon atoms.

Cross-linking agents with a SiH content of 1 to 15 mmol/g are used.

Salts, complexes and colloidal forms of the transition metals of the subgroup VIIIB of the periodic table are appropriate as catalysts c) for the hydrosilylation, preferably the metals platinum, palladium and rhodium; especially platinum complexes which are fabricated for example from hexachloroplatinic acid or from platinum salts prove to be appropriate.

The d) component is a microdispersed active filling material with a BET surface of at least 50 m$^2$/g like titanium dioxide, aluminium oxide, oxide of zinc and preferably wet precipitated or pyrogenically obtained silicic acid. The mentioned substances can exist as hydrophilic substances or substances made hydrophobic.

Furthermore, filling material in form of fibers or lamellae can be used as reinforcing filling material, whereby mineral filling material in form of fibers, like for example wollastonite and synthetic filling material in form of fibers, like for example glas fibers, ceramic fibers or plastic fibers, can be used.

The following are used as filling material e): metal oxides, metal hydroxides, metal oxide hydroxides, mixed oxides and mixed hydroxides, preferably silicon dioxide, especially in form of quartz and its crystalline modifications, translucent fused quartz as well as aluminium oxide, calcium oxide, aluminium hydroxide. Also filling material like calcium carbonate, diatomite, diatomaceous earth, French chalk, glass and filling material on synthetic base, for example polymethyl-methacrylate, polycarbonate, polyvinyl chloride, silicone resin powder, powder on the base of fluoro-organic compounds as well as organic and inorganic hollow balls, solid balls and fibers are appropriate. Furthermore, full or hollow synthetic particles, for example also in spherical form, on the surface of which inorganic filling material particles are embedded, can be used.

The filling material mentioned under d) and e) can also exist as surface coated material. The surface coating can be made for example with silanes and fatty acids which can present functional groups (for example vinyl, allyl, -SiH).

For the dyestuff mentioned under f), they are soluble dyestuff or pigment dyestuff. Food colours are preferably used in the field of dental medicine and medical applications of the silicone mass. Dyestuff pastes made of polysiloxane or mineral oil dyestuff formulations are also used.

Zeolites, anhydrous aluminium sulphate, molecular sieve, diatomite and blue gel can be used as moisture binder g).

Concerning the organopolysiloxanes mentioned under h) with more than two vinyl groups in the molecule, they are vinyl end stopped and vinyl side organopolysiloxanes with a viscosity of 20 to 350 000 mPa·s.

As inhibitors i) for the adjustment of reactivity of the hydrosilylation reaction, we use short chain organopolysiloxanes with the general formula $$CH_2=CH-SiR_2O-(SiR_2O)_n-SiR_2-CH=CH_2$$

in which R means similar or different hydrocarbon rests, eventually substituted, like for example alkyl, alkenyt, alkynyl and n=0 or a whole number between 1 and 6. R can still be an alkenyl or alkynyl terminated siloxane rest.

Furthermore, vinyl containing cyclic siloxanes, like for example tetravinyltetramethylcyclotetrasiloxane or organic hydroxyl compounds containing terminal double or triple bonds, can be used to adjust the cross-linking rate.

The under j) mentioned vinyl and ethoxyl group containing solid or liquid MQ-resins are characterized in that they contain the tetrafunctional $SiO_{4/2}$ as Q unit and the monofunctional $R3SiO_{1/2}$ as M constituents, whereby R=can be vinyl, methyl, ethyl or phenyl.

Moreover, there can also be as T units the trifunctional $RSiO_{3/2}$ and as D units the duofunctsonal with the same meaning for R as above.

These MQ-resins can be present in organopolysiloxanes with two or more vinyl groups in the molecule and with a viscosity of 21 to 350 000 mPa·s.

The vinyl group content of the mentioned MQ-resins is in the range of 0.1 to 8 mmol/g and the ethoxyl group content is lower than 4 mmol/g.

The SiOH content of the MQ-resins is so low that no gas evolution appears through hydrogen development. Moreover, the part of the volatile constituents of the MQ-resins is so low that the dimensional stability is not prejudiced.

The compounds k) which are used according to the invention are composed of organopolysiloxanes with two or more vinyl groups in the molecule and a viscosity of 21 to 350 000 mPa·s and the reinforcing filling material mentioned under d). This filling material is made hydrophobic in-situ by using modifying aids, for example hexamethyldisalazane.

Concerning the components l) used as tensides, emulsifying agents and stabilizing agents, they are anionic tensides, especially alkylsulphates, alkylbenzenesulfonates and alkyl-benzenephosphates, cationic tensides, especially tetraalkyl-ammoniumhalogenides, nonionic tensides, especially alkyl and alkylphenyl-polyalkylalkylene oxides and their alkylether and alkylester, fatty acid alkylolamides, saccharose fatty acid ester, trialkylaminoxides, silicone tensides or fluorotensides as well as amphoteric tensides, especially sulphatized or oxyethyiized condensation products made of alkylenphenols and formaldehyde, ethylene oxide-propylene oxide block polymers and modified polysiloxanes.

The tensides can also contain functional groups like for example OH—, —CH=CH$_2$, —OCO—(CH$_3$)C=CH$_2$ and SiH.

For the radio-opaque substances mentioned under m), they concern barium, strontium, lanthanum or zinc containing glass types, barium sulphate, zirconium dioxide, lanthanum oxide or ceramic filling material compositions which contain oxides of lanthanum, hafnium and rare-earth elements.

Furthermore, complex heavy metal fluorides with the general formula $M^{II}M^{IV}F_6$ or $YF_3$ can be used, whereby $M^{II}$ means a calcium, strontium or barium ion and $M^{IV}$ a titanium, zirconium or hafnium ion.

Moreover, atoms or atom groups combined with the silicone polymer which have radio-opaque properties like for example iodine combined with silicon.

For the H$_2$-absorbers/adsorbers mentioned under n), they concern microdispersed palladium or platinum or the alloys thereof which are eventually contained in aluminosilicates.

Furthermore, substances which eliminate or reduce the $H_2$ development can also be used, like for example 3-methyl-1-butyne-3-ol and $CH_3Si[O—C(CH_3)_2—C \equiv CH]_3$.

The silicone material according to the invention, i.e. the mixture of both components of the addition cross-linking two-component system, contains the following quantities of the single components a) to n) in percent in weight with respect to the whole silicone material:

a) 1 to 90% in weight, preferably 10 to 60% in weight, organopolysiloxanes with two vinyl groups in the molecule and a viscosity of 21 to 99 mPa·s
b) 1 to 40% in weight, preferably 1 to 20% in weight, organohydrogenpolysiloxanes
c) 0.0001 to 0.1% in weight, preferably 0.0005 to 0.1% in weight, catalysts for the acceleration of the hydrosilation reaction, related to pure metal
d) 0 to 80% in weight, preferably 0 to 50% in weight, za reinforcing filling material
e) 0 to 90% in weight, preferably 20 to 80% in weight, non-reinforcing filling material
f) 0 to 5% in weight, preferably 0 to 2% in weight, dyestuff
g) 0 to 30% in weight, preferably 0 to 5% in weight, moisture binder
h) 0 to 70% in weight, preferably 0 to 20% in weight, organopolysiloxanes with more than two vinyl groups per molecule
i) 0 to 1.0% in weight, preferably 0 to 0.1% in weight, inhibitors
j) 0 to 90% in weight, preferably 0 to 50% in weight, vinyl group containing MQ-resin
k) 0 to 80% in weight, preferably 0 to 50% in weight, compounds of vinyl group containing organopolysiloxanes and reinforcing filling material
l) 0 to 10% in weight, preferably 0 to 5% in weight, tensides, emulsifying agents and stabilizing agents
m) 0 to 90% in weight, preferably 0 to 80% in weight, radio-opaque substances
n) 0 to 20% in weight, preferably 0 to 10% in weight, $H_2$ absorbers/adsorbers or substances which reduce or eliminate the $H_2$ development.

The invention will be explained below in detail with examples in which all parts mean parts by weight.

EXAMPLE 1

125 parts of a vinyl end stopped polydimethylsiloxane with a viscosity of 50 mPa·s at 20° C. have been homogenized for 1.5 hours in a closed kneader with 330 parts aluminium hydroxide with a mean grain size of 10 µm, 15 parts of a pyrogenically fabricated microdispersed silicic acid made hydrophobic with a surface of 200 m²/g according to BET, 2 parts of a platinum catalyst with a content of pure platinum of 1% and vacuum degassed afterwards during 15 minutes.

We obtain a moderately fluid paste (DIN EN 24823). The paste is the A-component of the two-component silicone material according to the invention. After a storage at 230 C over 1 month, the viscosity and the reactivity were within the nominal range.

EXAMPLE 2

100 parts of a vinyl end stopped polydimethylsiloxane with a viscosity of 50 mPa·s at 20° C. have been homogenized for 1.5 hours in a closed kneader with 40 parts of a polymethylhydrogensiloxane with a viscosity of 30 mPa·s and a SiH content of 6.9 mmol/g, 350 parts aluminium hydroxide, 15 parts of a pyrogenically fabricated microdispersed silicic acid made hydrophobic with a surface of 200 m²/g according to BET and have been vacuum degassed afterwards during 15 minutes.

We obtain a moderately fluid paste (DIN EN 24823). The paste is the B-component of the two-component silicone material according to the invention. After a storage at 23° C. over 1 month, the viscosity and the reactivity were within the nominal range.

EXAMPLE 3

50 parts of the A-component described in example 1 and 50 parts of the B-component described in example 2 are squeezed out of a cartridge and homogeneously mixed in a static mixer.

The product remains processable for approximately 30 seconds at ambient temperature and is completely cured at a temperature of 35° C. within approx. 2 minutes after the beginning of the mixing.

We obtain hard moulded pieces which are hardly compressible as vulcanized material which can be purposefully broken off and which can be easily cut and processed with a miller. A Shore D hardness of 45 is obtained with the Shore D durometer 3100 of the Zwick company.

The modulus of elasticity in the compression test according to DIN 53457 is 36.8 MPa and in the tension test (DIN 53455) 45.0 MPa.

Test pieces : length 50 mm, diameter 10 mm, measuring length $I_o$ 15 mm, test pieces form: cylinder.

The modulus of elasticity is calculated as secant modulus between 0.1 and 0.8% elongation/compression according to the following equation:

$$E=[R(0.8\%)-R(0.1\%)]/(0.8\%-0.1\%).$$

EXAMPLE 4

125 parts of a vinyl end stopped polydimethylsiloxane with a viscosity of 25 mPa·s at 20° C. have been homogenized for 1.5 hours in a kneader with 330 parts of aluminium hydroxide with a mean grain size of 10 µm, 17 parts of a pyrogenically fabricated microdispersed silicic acid made hydrophobic with a surface of 200 m²/g according to BET, 3 parts of a platinum catalyst with a pure platinum content of 1% and have been vacuum degassed afterwards during 15 minutes.

We obtain a moderately fluid paste (DIN EN 24823). The paste is the A-component of the two-component silicone material according to the invention. After a storage at 23° C. over 1 month, the viscosity and the reactivity were within the nominal range.

EXAMPLE 5

100 parts of a vinyl end stopped polydimethylsiloxane with a viscosity of 25 mPa·s at 20° C. have been homogenized for 1.5 hours in a kneader with 45 parts of a polymethylhydrogensiloxane with a viscosity of 30 mPa·s and a SiH content of 6.9 mmol/g, 350 parts aluminium hydroxide, 17 parts of a pyrogenically fabricated microdispersed silicic acid made hydrophobic with a surface of 200 m²/g according to BET and have been vacuum degassed afterwards during 1 5 minutes.

We obtain a moderately fluid paste (DIN EN 24823). The paste is the B-component of the two-component silicone material according to the invention. After a storage at 23° C. over 1 month, the viscosity and the reactivity were within the nominal range.

EXAMPLE 6

50 parts of the A-component described in example 4 and 50 parts of the B-component described in example 5 are squeezed out of a cartridge and homogeneously mixed in a static mixer.

The product remains processable for approximately 30 seconds at ambient temperature and is completely cured at a temperature of 35° C. within approx. 2 minutes after the beginning of the mixing.

We obtain hard moulded pieces which are hardly compressible as vulcanized material which can be purposefully broken off and which can be easily cut and processed with a miller. A Shore D hardness of 53 is obtained with the Shore D durometer 3100 of the Zwick company.

The modulus of elasticity in the compression test according to DIN 53457 is 63,5 MPa and in the tension test (DIN 53455) 69,4 MPa.

Test pieces: length 50 mm, diameter 10 mm, measuring length $I_o$ 15 mm, test pieces form: cylinder.

The modulus of elasticity is calculated as secant modulus between 0,1 and 0,8% elongation/compression according to the following equation:

$$E=[R(0.8\%)-R(0.1\%)]/(0.8\%-0.1\%).$$

EXAMPLE 7 (COMPARISON EXAMPLE)

140 parts of a vinyl end stopped polydimethylsiloxane with a viscosity of 1000 mPa·s at 20° C. have been homogenized for 1.5 hours in a kneader with 10 parts of a vinyl group containing MQ-resin, solved in a vinyl end stopped polydimethylsiloxane with a overall viscosity of 6000 mPa·s, 10 parts of a pyrogenically produced microdispersed silicic acid made hydrophobic with a surface of 200 m²/g according to BET, 350 parts of aluminium hydroxide, 1.5 parts of a platinum catalyst with a pure platinum content of 1% and have been vacuum degassed afterwards for 15 minutes.

We obtain a moderately fluid paste (DIN EN 24823). The paste is the A-component of the two-component silicone material according to the invention. After a storage at 23° C. over 1 month, the viscosity and the reactivity were within the nominal range.

EXAMPLE 8 (COMPARISON EXAMPLE)

100 parts of a vinyl end stopped polydimethylsiloxane with a viscosity of 1000 mPa·s at 20° C. have been homogenized for 1.5 hours in a kneader with 10 parts of a vinyl group containing MQ-resin, solved in a vinyl end stopped polydimethylsiloxane with a overall viscosity of 6000 mPa·s, 40 parts of a polymethylhydrogensiloxane with a viscosity of 50 mPa·s and a SiH content of 2.3 mmol/g, 350 parts of aluminium hydroxide, 12 parts of a pyrogenically produced microdispersed silicic acid made hydrophobic with a surface of 200 m²/g according to BET and have been vacuum degassed afterwards for 15 minutes.

We obtain a moderately fluid paste (DIN EN 24823). The paste is the B-component of the two-component silicone material according to the invention. After a storage at 23° C. over 1 month, the viscosity and the reactivity were within the nominal range.

EXAMPLE 9 (COMPARISON EXAMPLE)

50 parts of the A-component described in example 7 and 50 parts of the B-component described in example 8 are squeezed out of a cartridge and homogeneously mixed in a static mixer.

The moulded pieces obtained as vulcanized material are moderately hard and elastically deformable. A Shore D hardness cannot be adequately measured. The Shore A hardness of 70 is obtained with the Shore A durometer of the Zwick company.

The modulus of elasticity in the compression test according to DIN 53457 is 4.4 MPa and in the tension test (DIN 53455) 5.0 MPa.

Test pieces : length 50 mm, diameter 10 mm, measuring length $I_o$ 15 mm, test pieces form: cylinder.

The modulus of elasticity is calculated as secant modulus between 0.1 and 0.8% elongation/compression according to the following equation:

$$E=[R(0.8\%)-R(0.1\%)]/(0.8\%-0.1\%).$$

These examples illustrate that the composition of the silicone material according to the invention has a decisive effect on hardness and modulus of elasticity of the resulting vulcanized material, whereby an extremely quick vulcanization is obtained during a practice-orientated processing time, i.e. the organopolysiloxanes according to the invention with two vinyl groups in the molecule and a viscosity of 21 to 99 mPa·s do not show any inhibiting effect, as will be shown in tables 1 and 2.

EXAMPLE 10 (COMPARISON EXAMPLE)

An usual commercial bite impression material on the base of addition cross-linking silicones is mixed according to the manufacturer's prescriptions and cured.

The Shore A hardness, measured with the Shore A durometer of the Zwick company, amounts to Shore A=85, the Shore D hardness amounts to Shore D=28.

The modulus of elasticity in the compression test according to DIN 53457 is 13.1 MPa and in the tension test (DIN 53455) 16.9 MPa.

This example will show that bite impression materials on the base of addition cross-linking silicones according to the state of the art have a considerably lower hardness or lower moduli of elasticity.

EXAMPLE 11 (COMPARISON EXAMPLE)

A transparent bite impression material (extra hard according to the manufacturer's indications) on the base of addition cross-linking silicones is mixed according to the manufacturer's prescriptions and cured.

The Shore A hardness, measured with the Shore A durometer of the Zwick company, amounts to Shore A=78, the Shore D hardness amounts to Shore D=19.

The modulus of elasticity in the compression test is 8.2 MPa (DIN 53457). The modulus of elasticity in the tension test is 8.6 MPa (DIN 53455).

TABLE 1

| Example n° | Shore A | Shore D | Modulus of elasticity Compression test | Modulus of elasticity Tension test |
|---|---|---|---|---|
| 3 | >95 | 45 | 36, 8 MPa | 45, 0 MPa |
| 6 | >95 | 53 | 63, 5 MPa | 69, 4 MPa |
| 9 | 70 | —*1 | 4, 4 MPa | 5, 0 MPa |
| 10 | 85 | 28 | 13, 1 MPa | 16, 9 MPa |
| 11 *2 | 78 | 19 | 8, 2 MPa | 8, 6 MPa |

*1 = cannot be appropriately measured
*2 = transparent product for sale (extra hard according to the manufacturer's indications) which results from the patent EP-A-0 522 341.

TABLE 2

| Example n° | Discharge force out of the cartridge | Processing time | Retention time in the mouth | Purposeful crushability | Ability to be cut with a miller |
|---|---|---|---|---|---|
| 3 | low | ≧30 sec. | 90 sec. | very good | very good |
| 6 | low | ≧30 sec. | 90 sec. | very good | very good |
| 9 | high | 60 sec. | 180 sec. | not possible | only limited |
| 10 | middle | ≦15 sec. | 90 sec. | possible | possible |
| 11 *2 | middle | ≧30 sec. | 210 sec. | not possible | only limited |

Shore D hardness in comparison
Example N° 3
Example N° 6
Example N° 9
Example N° 10
Example N° 11
(* cannot be appropriately measured)

What is claimed is:

1. Addition cross-linking two-component silicone materials based on polysiloxane comprising:
   a) organopolysiloxanes with two vinyl groups in the molecule, having a viscosity between 21 and 99 mPa·s and comprising substances of the general formula $CH_2=CH-SiR_2O-(SiR_2O)_n-SiR_2-CH=CH_2$, in which R is selected from the group consisting of alkyl, aryl, aralkyl, halogen-substituted alkyl, halogen-substituted aryl, cyanoalkyl, cycloalkyl, and cycloalkenyl, and wherein n is a whole number between 21 and 69,
   b) organohydrogenpolysiloxanes with two or more SiH groups in the molecule,
   c) hydrosilylation catalysts for the acceleration of a hydrosilylation reaction between the organopolysiloxanes of a) and the organohydrogenpolysiloxanes of b),
   d) reinforcing filling material,
   e) non reinforcing filling material,
   wherein after cross-linking via the hydrosilylation reaction the silicone materials have a Shore D hardness of greater than 35 and a modulus of elasticity of greater than 20 MPa.

2. Silicone materials according to claim 1, wherein the organohydrogenpolysiloxanes of b) are selected from the croup consisting of polyalkyl, polyaryl, polyalkylaryl, polvhalogenalkyl, polyhalogenaryl and polyhalogenalkylaryl siloxanes having a SiH content of 1 to 15 mmol/g.

3. Silicone materials according to claim 1, wherein the hydrosilylation catalysts of c) are selected from the group consisting of salts, complexes and colloidal forms of the transition metals of the subgroup VIII.

4. Silicone materials according to claim 1, wherein the reinforcing filling materials of d) are microdispersed active filling materials with a BET surface of at least 50 $m^2/g$ selected from the group consisting of titanium dioxide, aluminium oxide, oxide of zinc and wet precipitated or pyrogenically obtained silicic acid, wherein the reinforcing filling materials are hydrophilic or hydrophobic.

5. Silicone materials according to claim 1, wherein the reinforcing filling materials of d) are in form of mineral fibers or synthetic fibers or lamellae.

6. Silicone materials according to claim 1, wherein the non-reinforcing filling materials of e) are inorganic materials selected from the group consisting of metal oxides, metal hydroxides, metal oxide hydroxide, mixed oxides and mixed hydroxides, silicon dioxide in form of quartz and crystalline quartz modifications, translucent fused quartz, aluminium oxide, calcium oxide, aluminium hydroxide, calcium carbonate, diatomite, diatomaceous earth, French chalk, glass, or synthetic materials selected from the group consisting of polymethyl-methacrylate, polycarbonate, polyvinyl chloride, silicone resin powder, powder on the base of fluoro-organic compounds, organic and inorganic hollow balls, solid balls, fibers, and full or hollow synthetic particles, wherein the full or hollow synthetic particles have a surface with embedded inorganic filling material particles.

7. Silicone materials according to claim 1, wherein the filling materials of d) and e) are coated materials, wherein the coating is made of silanes and fatty acids which optionally have functional groups selected from the group consisting of vinyl, allyl, and SiH.

8. Silicone materials according to claim 1, wherein the silicone material optionally contains one or more of the following:
   f) a dyestuff;
   g) a moisture binder;
   h) organopolysiloxanes with more than two vinyl groups in the molecule;
   i) inhibitors for the adjustment of reactivity;
   j) vinyl and ethoxyl group containing solid or liquid MQ resins;
   k) compounds made of organopolysiloxanes and reinforcing filling material;
   l) tensides, emulsifying agents and stabilizing agents;
   m) radiopaque substances;
   n) $H_2$-absorbers/adsorbers or substances which eliminate or reduce $H_2$-development.

9. Silicone materials according to claim 8, wherein the dyestuff of f) are selected from the group consisting of soluble dyestuff, pigment dyestuff, food colours, and dyestuff pastes made of polysiloxane dyestuff formulations or mineral oil dyestuff formulations.

10. Silicone materials according to claim 8, wherein the moisture binder of g) is selected from the group consisting of zeolites, anhydrous aluminium sulphate, molecular sieve, diatomite and blue gel.

11. Silicone materials according to claim 8, wherein the organopolysiloxanes of h) are vinyl end stopped and have vinyl groups in side chains, wherein the organopolysiloxanes of h) have a viscosity of 20 to 350 000 mPa·s.

12. Silicone materials according to claim 8, wherein the inhibitors of i) are short chain organopolysiloxanes with the general formula $CH_2=CH-SiR2O-(SiR_2O)_n-SiR_2-CH=CH_2$, in which R means similar or different hydrocarbon rests, optionally substituted, selected from the group consisting of alkyl, alkenyl, alkynyl or means a siloxane rest terminated by alkenyl or alkynyl, wherein n[=0] is zero or a whole number between 1 and 6.

13. Silicone materials according to claim 8, wherein the inhibitors of i) are vinyl containing cyclic siloxanes or organic hydroxyl compounds containing terminal or triple bonds.

14. Silicone materials according to claim 13, wherein the vinyl containing cyclic siloxane is tetravinyl tetramethyl cyclotetrasiloxane.

15. Silicone materials according to claim 8, wherein the vinyl and ethoxyl group containing solid or liquid MQ resins of j) have Q units containing tetrafunctional $SiO_{4/2}$ and M constituents having monofunctional $R_3SiO_{1/2}$, wherein R is selected from the group consisting of vinyl, methyl, ethyl, and phenyl.

16. Silicone materials according to claim 15, wherein the vinyl and ethoxyl group containing solid or liquid MQ-resins contain T-units and D-units, wherein the T-units are trifunctional $RSiO_{3/2}$ and the D-units are duofunctional $R_2SiO_{1/2}$, wherein R is selected from the group consisting of vinyl, methyl, ethyl, and phenyl.

17. Silicone materials according to claim 15, wherein MQ-resins are present dissolved in organopolysiloxanes with two or more vinyl groups in the molecule and a viscosity of 21 to 350 000 mPa·s, wherein the vinyl group content of the MQ-resins is in the range of 0.1 to 8 mmol/g and the ethoxyl group content is lower than 4 mmol/g.

18. Silicone materials according to claim 15, wherein the SiOH content of the MQ-resins is so low that no hydrogen gas development occurs in the Presence of the organohydrogenpolysiloxanes and of the hydrosilylation catalysts, wherein the contents of volatile constituents of the MQ-resins is so low that the dimensional stability of the silicone materials after cross-linking is not compromised when used in dental applications.

19. Silicone materials according to claim 8, wherein the compounds of k) comprise organopolysiloxanes with two or more vinyl groups in the molecule and a viscosity of 21 to 350 000 mPa·s and comprise filling material of the type of the reinforcing filling material of d), wherein this filling material is made hydrophobic by using modifying aids.

20. Silicone materials according to claim 8, wherein the radiopaque substances are selected from the group consisting of barium; strontium; lanthanum containing glass types; zinc containing glass types; barium sulphate; zirconium dioxide; lanthanum oxide; ceramic filling material compositions which contain oxides of lanthanum, hafnium, and rare-earth elements; complex heavy metal fluorides with the general formula $M^{II}M^{IV}F_6$ wherein $M^{II}$ means a calcium, strontium, or barium ion and $M^{IV}$ a titanium, zirconium or hafnium ion; $YF_3$; and silicone polymers containing atoms or atom groups having radiopaque properties.

21. Silicone materials according to claim 8, wherein the $H_2$-absorbers/adsorbers of n) are selected from the group consisting of microdispersed palladium, platinum, and the alloys thereof which are optionally contained in aluminosilicates, and wherein the substances of n) which eliminate or reduce the H2-development are 3-methyl-1-butyne-3-ol and $CH_3Si[O—C(CH_3)_2—C≡CH]_3$.

22. Silicone materials according to claim 8, containing the following quantities of a) to n) in percent by weight with respect to the whole silicone material:
a) 1 to 90% by weight organopolysiloxanes,
b) 1 to 40% by weight organohydrogenpolysiloxanes,
c) 0.0001 to 0.1% by weight catalysts for the acceleration of the hydrosilylation reaction, wherein the amount in % by weight refers to the pure metal of the catalysts,
d) more than 0% up to 80% by weight reinforcing filling material,
e) more than 0% up to 90% by weight non-reinforcing filling material,
f) 0 to 5% by weight dyestuff,
g) 0 to 30% by weight moisture binder,
h) 0 to 70% by weight organopolysiloxanes with more than two vinyl groups in the molecule,
i) 0 to 1.0% by weight inhibitors,
j) 0 to 90% by weight vinyl and ethoxyl group containing MQ-resins,
k) 0 to 80% by weight compounds of organopolysiloxanes and reinforcing filling material, wherein the organopolysiloxanes contain vinyl groups,
l) 0 to 10% by weight tensides, emulsifying agents and stabilizing agents,
m) 0 to 90% by weight radiopaque substances
n) 0 to 20% by weight $H_2$, absorbers/adsorbers or substances which reduce or eliminate the $H_2$ development.

23. Silicone materials according to claim 1, wherein the tensides, emulsifying agents and stabilizing agents of l) are selected from the group consisting of anionic tensides, cationic tensides, nonionic tensides, silicone tensides, fluorotensides, amphoteric tensides.

24. Silicone materials according to claim 23, wherein the anionic tensides are selected from the group consisting of alkyl sulphates, alkylbenzene-sulfonates and alkylbenzene-phosphates; wherein the cationic tensides are tetraalkylammoniumhalogenides; wherein the nonionic tensides are selected from the group consisting of alkyl and alkylphenylpolyalkylalkylene oxides and their alkylether and alkylesters, fatty acid alkylolamides, saccharose fatty acid ester, and trialkylamine oxides; wherein the amphoteric tensides are selected from the group consisting of sulphatized or oxyethylized condensation products made of alkylenephenols and formaldehyde, ethylene oxide-propylene oxide block polymers and polysiloxanes.

25. Silicone materials according to claim 24, wherein the tensides contain functional groups selected from the group consisting of $OH—$, $—CH═CH_2$, $—OCO—(CH_3)C═CH_2$, and $SiH$.

26. Silicone materials according to claim 1, wherein alkyl is methyl, ethyl or isopropyl; wherein aryl is phenyl, naphthyl, tolyl or xylyl; wherein aralkyl is benzyl or phenylethyl; wherein halogen substituted alkyl is 3,3,3-trifluoropropyl; and wherein halogen substituted aryl is chlorophenyl or difluorophenyl.

27. Silicone materials according to claim 3, wherein the hydrosilylation catalyst comprises a metal selected from the group consisting of platinum, palladium, and rhodium.

28. Silicone materials according to claim 27, wherein the hydrosilylation catalyst is a platinum complex made from hexachloroplatinic acid or from platinum salts.

29. Silicone materials according to claim 5, wherein the mineral or synthetic fibers are selected from the group consisting of wollastonite, glass fibers, ceramic fibers, and plastic fibers.

30. Silicone materials according to claim 22, containing the following quantities of a) to n) in percent by weight with respect to the whole silicone material:
a) 10 to 60% by weight organopolysiloxanes,
b) 1 to 20% by weight organohydrogenpolysiloxanes,
c) 0.0005 to 0.1% by weight catalysts,
d) more than 0% up to 50% by weight reinforcing filling material,
e) 20 to 80% by weight non-reinforcing filling material,
f) 0 to 2% by weight dyestuff,
g) 0 to 5% by weight moisture binder,
h) 0 to 20% by weight organopolysiloxanes with more than two vinyl groups in the molecule,
i) 0 to 0.1% by weight inhibitors,
j) 0 to 50% by weight vinyl and ethoxyl group containing MQ-resins,
k) 0 to 50% by weight compounds of organopolysiloxanes and reinforcing filling material,
l) 0 to 5% by weight tensides, emulsifying agents, and stabilizing agents,
m) 0 to 80% by weight radiopaque substances,
n) 0 to 10% by weight $H_2$ absorbers/absorbers or substances which reduce or eliminate the $H_2$ development.

31. A bite impression material in dental medicine and dental technique comprised of the silicone materials according to claim 1.

* * * * *